US010975001B2

(12) United States Patent
Miyamoto et al.

(10) Patent No.: US 10,975,001 B2
(45) Date of Patent: Apr. 13, 2021

(54) METHOD FOR PRODUCING ALPHA-OLEFIN OLIGOMER (71) Applicant: IDEMITSU KOSAN CO., LTD., Chiyoda-ku (JP)

(72) Inventors: Shinji Miyamoto, Ichihara (JP); Naoya Kawano, Sodegaura (JP); Tuan Anh Tran, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

(21) Appl. No.: 16/349,854

(22) PCT Filed: Nov. 15, 2017

(86) PCT No.: PCT/JP2017/041081
§ 371 (c)(1),
(2) Date: May 14, 2019

(87) PCT Pub. No.: WO2018/092803
PCT Pub. Date: May 24, 2018

(65) Prior Publication Data
US 2020/0055798 A1 Feb. 20, 2020

(30) Foreign Application Priority Data
Nov. 18, 2016 (JP) .............................. JP2016-225048

(51) Int. Cl.
*C07C 2/22* (2006.01)
*C07C 7/04* (2006.01)
(Continued)

(52) U.S. Cl.
CPC ................. *C07C 2/22* (2013.01); *C07C 7/04* (2013.01); *C07C 2/04* (2013.01); *C07C 2/06* (2013.01);
(Continued)

(58) Field of Classification Search
CPC .... C07C 2/22; C07C 7/04; C07C 2/06; C07C 2/04; C07C 2/08; C07C 2527/135;
(Continued)

(56) References Cited

U.S. PATENT DOCUMENTS 5,750,816 A * 5/1998 Araki .................. B01J 31/0237
585/512
2003/0027947 A1* 2/2003 Kobayashi ................ C07C 2/30
526/70

(Continued)

FOREIGN PATENT DOCUMENTS

JP 2-178234 A 7/1990
JP 2002-255864 A 9/2002

(Continued)

OTHER PUBLICATIONS

Japanese Office Action dated Apr. 28, 2020 in Patent Application No. 2016-225048 (with English translation), 5 pages.

(Continued)

*Primary Examiner* — Ali Z Fadhel
(74) *Attorney, Agent, or Firm* — Oblon, McClelland, Maier & Neustadt, L.L.P.

(57) ABSTRACT

A method for producing an α-olefin oligomer, the method including subjecting α-olefin to oligomerization reaction to produce an α-olefin oligomer mixture, carrying out distillation separation of α-olefin oligomer having less than n carbon atoms in the mixture to obtain a distillation residue containing α-olefin oligomer having n or more carbon atoms, and then carrying out a step of removing high molecular weight molecules from the distillation residue.

11 Claims, 3 Drawing Sheets (51) Int. Cl.
*C07C 2/06* (2006.01)
*C07C 2/04* (2006.01)
*C07C 2/08* (2006.01)
(52) U.S. Cl.
CPC .......... *C07C 2/08* (2013.01); *C07C 2527/135* (2013.01); *C07C 2531/14* (2013.01)
(58) Field of Classification Search
CPC . C07C 2531/14; C07C 2531/38; C07C 7/005; C07C 2/88; C08F 6/04; C08F 6/12; C08F 10/00; C07B 61/00
See application file for complete search history.

(56) References Cited

U.S. PATENT DOCUMENTS

| 2004/0127614 | A1* | 7/2004 | Jiang | ...................... | C09J 123/12 524/270 |
| 2010/0036185 | A1 | 2/2010 | Yokoyama et al. | | |
| 2013/0296483 | A1 | 11/2013 | Yokota et al. | | |
| 2014/0275669 | A1* | 9/2014 | Daage | ...................... | C07C 2/12 585/251 |
| 2018/0009728 | A1* | 1/2018 | Emoto | ...................... | C08F 6/12 |

FOREIGN PATENT DOCUMENTS

| JP | 2002-256007 A | 9/2002 |
| JP | 2008-178873 A | 8/2008 |
| JP | 2012-70655 A | 4/2012 |
| WO | WO 02/051777 A1 | 7/2002 |
| WO | WO 2008/081646 A1 | 7/2008 |
| WO | WO 2012/096159 A1 | 7/2012 |
| WO | WO 2015/050220 A1 | 4/2015 |

OTHER PUBLICATIONS

International Search Report dated Dec. 26, 2017 in PCT/JP2017/041081 filed Nov. 15, 2017.

Office Action dated Jun. 20, 2020 in corresponding Iranian Patent Application No. 139850140003001417 (with English Translation), 14 pages.

Written Opinion dated Jun. 4, 2020 in corresponding Singaporean Patent Application No. 11201904324X, 6 pages.

* cited by examiner

METHOD FOR PRODUCING ALPHA-OLEFIN OLIGOMER

TECHNICAL FIELD

The present invention relates to a method for producing an α-olefin oligomer having a low cloud point.

BACKGROUND ART

α-Olefin oligomer is a useful substance widely used as a starting monomer material for olefin polymers, as a comonomer for a variety of high molecular polymers, and also as a starting material for plasticizers, surfactants, and the like.

Among α-olefin oligomers, ethylenic oligomers have been intensively studied for their production methods. In general, for example, ethylene (C2) is oligomerized using a Ziegler-based catalyst to obtain a mixture of C4 to C20 ethylenic oligomers such as butene (C4), hexene (C6), and octene (C8), or C20 or higher ethylenic oligomers, and then individual ethylenic oligomers are isolated by distillation in the order of the number of carbon atoms such that components with smaller numbers of carbon atoms are first isolated using a plurality of distillation columns. More specifically, the mixture of ethylenic oligomers is distilled to separate a mixture of C6 and lower ethylenic oligomers and a mixture of C8 and higher ethylenic oligomers from each other. Subsequently, the mixture of C6 and lower ethylenic oligomers is subjected to distillation to allow separation into C4 oligomer alone and C6 oligomer alone. The mixture of C8 and higher ethylenic oligomers is subjected to distillation to allow isolation of C8 alone at the top, and withdrawal of a mixture of C10 and higher ethylenic oligomers as a distillation residue from the bottom. Thereafter, the mixture of C10 and higher ethylenic oligomers is subjected to distillation under conditions with a higher distillation temperature to allow isolation of C10 alone at the top, and withdrawal of a mixture of C12 and higher as a distillation residue at the bottom. By repeating such a distillation operation, ethylenic oligomers having numbers of carbon atoms varying at intervals of two can be isolated (PTLs 1 to 3). However, as the number of carbon atoms in an ethylenic oligomer increases, the boiling point increases, so that isolation of the ethylenic oligomer by distillation under temperature conditions in which degradation can be avoided becomes difficult even under reduced pressure.

For example, it is known that separation of C26 ethylenic oligomer from ethylenic oligomers having numbers of carbon atoms larger than the oligomer is generally difficult, and that separation of C28 or higher, or C30 or higher ethylenic oligomer from ethylenic oligomers having numbers of carbon atoms larger than the oligomer is more difficult.

CITATION LIST

Patent Literatures

PTL 1: WO 2002/051777
PTL 2: JP 2002-255864 A
PTL 3: JP 2002-256007 A

SUMMARY OF INVENTION

Technical Problem

As described above, for the mixture of ethylenic oligomers obtained as a distillation residue withdrawn at the bottom of the distillation column, isolation of ethylenic oligomers having the respective numbers of carbon atoms by distillation becomes difficult when the number of carbon atoms exceeds a particular number. Since the mixture of ethylenic oligomers obtained as a distillation residue has a high cloud point, it cannot be easily handled, and its use as a wax is difficult. Because of such reasons, the mixture of ethylenic oligomers obtained as a distillation residue is subjected to decomposition in a catalytic cracking apparatus (FCC apparatus) to be converted into a base of gasoline, or is used simply as a fuel, and thus, the use is limitative and there is a problem of lowered value in use.

In particular, further distillation separation of a mixture of C26 and higher ethylenic oligomers (which may be hereinafter simply referred to as C26+) or a mixture of C28 and higher, or C30 and higher components (which may be hereinafter simply referred to as C28+ or C30+) withdrawn at the bottom is generally considered to be difficult, so that lowering of the cloud point is demanded.

Solution to Problem

In view of such circumstances, the present inventors intensively have studied and as a result, have found out that a small amount of high molecular weight molecules contained in the mixture of ethylenic oligomers obtained as a distillation residue are a cause of the high cloud point. Based on such a knowledge, the present inventors have found out that by removing the small amount of high molecular weight molecules contained in the mixture of ethylenic oligomers obtained as a distillation residue, the cloud point can be lowered and properties of handling as a wax can be improved.

More specifically, the present invention relates to the following [1] to [10].

[1] A method for producing an α-olefin oligomer, including: subjecting α-olefin to oligomerization reaction to produce an α-olefin oligomer mixture, carrying out distillation separation of α-olefin oligomer having less than n carbon atoms in the mixture to obtain a distillation residue containing α-olefin oligomer having n or more carbon atoms, and then carrying out a step of removing high molecular weight molecules from the distillation residue.

[2] The method for producing an α-olefin oligomer according to [1], wherein the oligomerization reaction of α-olefin is carried out in an organic solvent in the presence of a Ziegler-based catalyst.

[3] The method for producing an α-olefin oligomer according to [1] or [2], wherein the α-olefin is ethylene.

[4] The method for producing an α-olefin oligomer according to any one of [1] to [3], wherein the number of carbon atoms n is 26 or 30.

[5] The method for producing an α-olefin oligomer according to any one of [1] to [4], wherein the high molecular weight molecules have a weight average molecular weight of 100,000 or more.

[6] The method for producing an α-olefin oligomer according to any one of [1] to [5], wherein the step of removing high molecular weight molecules from the distillation residue is a step of removing high molecular weight molecules by thin film distillation of the distillation residue.

[7] The method for producing an α-olefin oligomer according to [6], wherein, in the thin film distillation, the distillation temperature is from 150 to 320° C., and the pressure is from $1.0 \times 10^{-2}$ to $5.0 \times 10^{-2}$ Torr.

[8] The method for producing an α-olefin oligomer according to [6] or [7], wherein the thin film distillation is short-path distillation.

[9] The method for producing an α-olefin oligomer according to any one of [1] to [5], wherein the step of removing high molecular weight molecules from the distillation residue is a step of dissolving the distillation residue in an organic solvent under heat, cooling the resulting solution to allow formation of a precipitate, and then removing the precipitate.

[10] The method for producing an α-olefin oligomer according to [9], wherein the temperature under heat is from 70 to 130° C.; the retention time under heat is from 0.5 to 2 hours; the cooling rate under cooling is from 0.1 to 5° C./minute; and the retention time after cooling is from 0 to 1 hour.

Advantageous Effects of Invention

The α-olefin oligomer obtained by the method for producing an α-olefin oligomer of the present invention has a low cloud point, and therefore, the α-olefin oligomer can be easily handled and is highly useful as a wax.

DESCRIPTION OF EMBODIMENTS

The present invention is a method for producing an α-olefin oligomer, the method including subjecting α-olefin to oligomerization reaction to produce an α-olefin oligomer mixture, carrying out distillation separation of α-olefin oligomer having less than n carbon atoms in the mixture to obtain a distillation residue containing α-olefin oligomer having n or more carbon atoms, and then carrying out a step of removing high molecular weight molecules from the distillation residue.

The method for producing an α-olefin oligomer of the present invention is described below.

(Production of α-Olefin Oligomer Mixture)

In the present invention, the α-olefin oligomer mixture can be obtained by, for example, polymerization of α-olefin in the presence of a Ziegler-based catalyst. The Ziegler-based catalyst contains a combination of (A) a transition metal compound and (B) an organoaluminum, and, in addition, (C) a third component to be used as desired. As the (A) transition metal compound, a compound represented by the following general formula may be used:

$$MX_xY_yO_z \qquad (I)$$

wherein M represents a zirconium atom or a titanium atom; X represents a halogen atom (chlorine atom, bromine atom, or iodine atom); Y represents RO—, $R_2N$—, —OCOR, —OSO$_3$R, R—, —Cp (cyclopentadienyl) (where R is a linear or branched alkyl group having 1 to 20 carbon atoms), or a β diketonato represented by formula (II):

wherein in the formula (II), $R^1$, $R^2$ and $R^3$ each independently represent a hydrogen atom, an alkyl group having 1 to 20 carbon atoms, or an alkyl group which is substituted with a halogen atom and which has 1 to 20 carbon atoms, with the proviso that one of $R^1$, $R^2$ and $R^3$ is an alkyl group which is substituted with a halogen atom and which has 1 to 20 carbon atoms; and x, y, and z each represent an integer of 0 to 4, with the proviso that x+y+z=4.

Specific examples of such a compound include ZrCl$_4$, ZrBr$_4$, ZrI$_4$, ZrBrCl$_3$, ZrBr$_2$Cl$_2$, TiCl$_4$, TiBr$_4$, TiI$_4$, TiBrCl$_3$, TiBr$_2$Cl$_2$, Zr(OC$_2$H$_5$)$_4$, Zr(OC$_2$H$_5$)$_2$Cl$_2$, Zr(O-n-C$_3$H$_7$)$_4$, Zr(O-n-C$_3$H$_7$)$_2$Cl$_2$, Zr(O-iso-C$_3$H$_7$)$_4$, Zr(O-iso-C$_3$H$_7$)$_2$Cl$_2$, Zr(O-n-C$_4$H$_9$)$_4$, Zr(O-n-C$_4$H$_9$)$_2$Cl$_2$, Zr(O-iso-C$_4$H$_9$)$_4$, Zr(O-iso-C$_4$H$_9$)$_2$Cl$_2$, Zr(O-tert-C$_4$H$_9$)$_4$, Zr(O-tert-C$_4$H$_9$)$_2$Cl$_2$, Zr((CH$_3$)$_2$N)$_4$, Zr((C$_2$H$_5$)$_2$N)$_4$, Zr((n-C$_3$H$_7$)$_2$N)$_4$, Zr((iso-C$_3$H$_7$)$_2$N)$_4$, Zr((n-C$_4$H$_9$)$_2$N)$_4$, Zr((tert-C$_4$H$_9$)$_2$N)$_4$, Zr(OSO$_3$CH$_3$)$_4$, Zr(OSO$_3$C$_2$H$_5$)$_4$, Zr(OSO$_3$C$_3$H$_7$)$_4$, Zr(OSO$_3$C$_4$H$_9$)$_4$, ZrCp$_2$Cl$_2$, ZrCp$_2$ClBr, Ti(OC$_2$H$_5$)$_4$, Ti(OC$_2$H$_5$)$_2$Cl$_2$, Ti(O-n-C$_3$H$_7$)$_4$, Ti(O-n-C$_3$H$_7$)$_2$Cl$_2$, Ti(O-iso-C$_3$H$_7$)$_4$, Ti(O-iso-C$_3$H$_7$)$_2$Cl$_2$, Ti(O-n-C$_4$H$_9$)$_4$, Ti(O-n-C$_4$H$_9$)$_2$Cl$_2$, Ti(O-iso-C$_4$H$_9$)$_4$, Ti(O-iso-C$_4$H$_9$)$_2$Cl$_2$, Ti(O-tert-C$_4$H$_9$)$_4$, Ti(O-tert-C$_4$H$_9$)$_2$Cl$_2$, Ti((CH$_3$)$_2$N)$_4$, Ti((C$_2$H$_5$)$_2$N)$_4$, Ti((n-C$_3$H$_7$)$_2$N)$_4$, Ti((iso-C$_3$H$_7$)$_2$N)$_4$, Ti((n-C$_4$H$_9$)$_2$N)$_4$, Ti((tert-C$_4$H$_9$)$_2$N)$_4$, Ti(OSO$_3$CH$_3$)$_4$, Ti(OSO$_3$C$_2$H$_5$)$_4$, Ti(OSO$_3$C$_3$H$_7$)$_4$, Ti(OSO$_3$C$_4$H$_9$)$_4$, TiCp$_2$Cl$_2$, TiCp$_2$ClBr, Zr(OCOC$_2$H$_5$)$_4$, Zr(OCOC$_2$H$_5$)$_2$Cl$_2$, Zr(OCOC$_3$H$_7$)$_4$, Zr(OCOC$_3$H$_7$)$_2$Cl$_2$, Zr(OCOC$_3$H$_7$)$_4$, Zr(OCOC$_3$H$_7$)$_2$Cl$_2$, Zr(OCOC$_4$H$_9$)$_4$, Zr(OCOC$_4$H$_9$)$_2$Cl$_2$, Ti(OCOC$_2$H$_5$)$_4$, Ti(OCOC$_2$H$_5$)$_2$Cl$_2$, Ti(OCOC$_3$H$_7$)$_4$, Ti(OCOC$_3$H$_7$)$_2$Cl$_2$, Ti(OCOC$_3$H$_7$)$_4$, Ti(OCOC$_3$H$_7$)$_2$Cl$_2$, Ti(OCOC$_4$H$_9$)$_4$, Ti(OCOC$_4$H$_9$)$_2$Cl$_2$, ZrCl$_2$(HCOCFCOF)$_2$, and ZrCl$_2$(CH$_3$COCFCOCH$_3$)$_2$.

Examples of the organoaluminum (B) include a compound represented by general formula:

$$AlY_aX_bO_cN_d \qquad (III)$$

wherein X represents a halogen atom (chlorine atom, bromine atom, or iodine atom); Y represents RO—, $R_2N$—, —OCOR, or R— (where R represents a linear or branched alkyl group having 1 to 20 carbon atoms); and a, b, c, and d each represent an integer of 0 to 3, with the proviso that a+b+c+d=3, and/or a compound represented by general formula:

$$Al_2Y_{a'}X_{b'}O_{c'}N_{d'} \qquad (IV)$$

wherein X represents a halogen atom (chlorine atom, bromine atom, or iodine atom); Y represents RO—, $R_2N$—, —OCOR, —RCOCR', COR'', or R— (where R, R' and R'' each represent a linear or branched alkyl group having 1 to 20 carbon atoms); and a', b', c', and d' each represent an integer of 0 to 6, with the proviso that a'+b'+c'+d'=6.

Examples of the compound represented by the general formula (III) include Al(CH$_3$)$_3$, Al(C$_2$H$_5$)$_3$, Al(C$_3$H$_7$)$_3$, Al(iso-C$_3$H$_7$)$_3$, Al(C$_4$H$_9$)$_3$, Al(iso-C$_4$H$_9$)$_3$, Al(C$_5$H$_{11}$)$_3$, Al(C$_6$H$_{13}$)$_3$, Al(C$_8$H$_{17}$)$_3$, Al(C$_2$H$_5$)$_2$Cl, Al(C$_2$H$_5$)$_2$Br, Al(C$_2$H$_5$)$_2$I, Al(C$_2$H$_5$)Cl$_2$, Al(C$_2$H$_5$)Br$_2$, Al(C$_2$H$_5$)I$_2$, AlC$_2$H$_5$(OC$_2$H$_5$)$_2$, AlC$_2$H$_5$(OC$_3$H$_7$)$_2$, AlC$_2$H$_5$(OC$_4$H$_9$)$_2$, Al(OC$_2$H$_5$)$_2$Cl, Al(OC$_3$H$_7$)$_2$Cl, Al(OC$_4$H$_9$)$_2$Cl, Al(OC$_2$H$_5$)Cl$_2$, Al(OC$_3$H$_7$)Cl$_2$, Al(OC$_4$H$_9$)Cl$_2$, AlC$_2$H$_5$(OCOC$_2$H$_5$)$_2$, AlC$_2$H$_5$(OCOC$_3$H$_7$)$_2$, AlC$_2$H$_5$(OCOC$_4$H$_9$)$_2$, Al(OCOC$_2$H$_5$)$_2$ Cl, Al(OCOC$_3$H$_7$)$_2$Cl, Al(OCOC$_4$H$_9$)$_2$Cl, Al(OCOC$_2$H$_5$)Cl$_2$, Al(OCOC$_3$H$_7$)Cl$_2$, Al(OCOC$_4$H$_9$)Cl$_2$, Al(C$_2$H$_5$)$_2$OC$_2$H$_5$, Al(C$_2$H$_5$)$_2$OC$_3$H$_7$, Al(C$_2$H$_5$)$_2$OC$_4$H$_9$, Al(C$_2$H$_5$)$_2$(N(C$_2$H$_5$)$_2$), Al(C$_2$H$_5$)$_2$(N(C$_3$H$_7$)$_2$), and Al(C$_2$H$_5$)$_2$ N(C$_4$H$_9$)$_2$.

Examples of the compound represented by the general formula (IV) include Al$_2$(CH$_3$)$_3$Cl$_3$, Al$_2$(CH$_3$)$_3$Br$_3$, Al$_2$(C$_2$H$_5$)$_3$Cl$_3$, Al$_2$(C$_2$H$_5$)$_3$Br$_3$, Al$_2$(C$_2$H$_5$)$_3$I$_3$, Al$_2$(C$_2$H$_5$)$_3$BrCl$_2$, Al$_2$(C$_3$H$_7$)$_3$Cl$_3$, Al$_2$(iso-C$_3$H$_7$)$_3$Cl$_3$, Al$_2$(C$_4$H$_9$)$_3$Cl$_3$, Al$_2$(iso-C$_4$H$_9$)$_3$Cl$_3$, Al$_2$(C$_5$H$_{11}$)$_3$Cl$_3$, Al$_2$(C$_8$H$_{17}$)$_3$Cl$_3$, Al$_2$(C$_2$H$_5$)$_2$(CH$_3$)Cl$_3$, Al$_2$(OC$_2$H$_5$)$_3$Cl$_3$, Al$_2$(OC$_3$H$_7$)$_3$Cl$_3$, Al$_2$(OC$_4$H$_9$)$_3$Cl$_3$, Al$_2$(OCOC$_2$H$_5$)$_3$Cl$_3$, Al$_2$(OCOC$_3$H$_7$)$_3$Cl$_3$, and Al$_2$(OCOC$_4$H$_9$)$_3$Cl$_3$.

As the third component (C), which is used as desired, at least one compound selected from sulfur compounds, phosphorus compounds, and nitrogen compounds may be used. The third component contributes to improvement of the purity of the α-olefin oligomer as the objective product. The sulfur compound is not limited as long as it is an organosulfur compound, and preferred examples of the sulfur compound include thioethers such as dimethyl sulfide, diethyl sulfide, dipropyl sulfide, dihexyl sulfide, dicyclohexyl sulfide, and diphenyl thioether; dialkyl disulfide compounds such as dimethyl disulfide, diethyl disulfide, dipropyl disulfide, dibutyl disulfide, dihexyl disulfide, dicyclohexyl disulfide, and ethylmethyl disulfide; thiophenes such as thiophene, 2-methylthiophene, 3-methylthiophene, 2,3-dimethylthiophene, 2-ethylthiophene, and benzothiophene, and heterocyclic sulfur compounds such as tetrahydrothiophene and thiopyrane; aromatic sulfur compounds such as diphenyl sulfide, diphenyl disulfide, methylphenyl disulfide, and methylphenyl sulfide; thiourea; and sulfides such as methyl sulfide, ethyl sulfide, and butyl sulfide.

The phosphorus compound is not limited as long as it is an organophosphorus compound, and preferred examples of the phosphorus compound include phosphines such as triphenylphosphine, triethylphosphine, tributylphosphine, tripropylphosphine, trioctylphosphine, and tricyclohexylphosphine. The nitrogen compound is not limited as long as it is an organonitrogen compound, and preferred examples of the nitrogen compound include organic amines such as methylamine, ethylamine, propylamine, butylamine, pentylamine, hexylamine, cyclohexylamine, octylamine, decylamine, aniline, benzylamine, naphthylamine, dimethylamine, diethylamine, dibutylamine, diphenylamine, methylphenylamine, trimethylamine, triethylamine, tributylamine, triphenylamine, pyridine, and picoline.

In the present invention, among the various sulfur compounds, phosphorus compounds, and nitrogen compounds, one or more compounds selected from, for example, dimethyl disulfide, thiophenes, thiourea, triphenylphosphine, tributylphosphine, trioctylphosphine, and aniline may be preferably used.

The polymerization reaction of α-olefin is preferably carried out in an organic solvent. Examples of the organic solvent include alicyclic compounds such as cyclohexane and decalin; aromatic hydrocarbons such as benzene, toluene, xylene, chlorobenzene, ethylbenzene, dichlorobenzene, and chlorotoluene, and halides thereof; aliphatic hydrocarbons such as pentane, hexane, heptane, octane, nonane, and decane; and halogenated aliphatic hydrocarbons such as dichloroethane and dichlorobutane.

The blending ratio among the components (A), (B), and (C) in the organic solvent in the present invention is as follows. In terms of the amount in 250 mL of the organic solvent, the amount of component (A) is usually 0.01 to 5 mmol, preferably 0.03 to 1 mmol. The amount of component (B) is usually 0.05 to 15 mmol, preferably 0.06 to 3 mmol. The amount of component (C) is usually 0.05 to 20 mmol; in the case where the sulfur compound is used as the component (C), the amount is preferably 0.1 to 10 mmol; in the case where the nitrogen compound or the phosphorus compound is used as the component (C), the amount is preferably 0.05 to 5 mmol. With respect to the blending ratio between the components (A) and (B), when Al/Zr or Ti (molar ratio) is set to fall within the range of 1 to 15, an even more preferred result can be obtained.

The polymerization reaction of the α-olefin oligomer mixture in the present invention is carried out usually at a temperature of 100 to 150° C. under a pressure of 30 to 90 kg/cm$^2$·G (2.94 to 8.82 MPa). While the reaction time varies depending on the temperature and pressure and cannot be specified in a uniform manner, a reaction time of about 10 minutes to 60 minutes is usually sufficient.

In the production method of the present invention, the α-olefin used as a starting material is preferably α-olefin having 2 to 4 carbon atoms, more preferably ethylene.

In the case where ethylene is used as a starting material, the ethylenic oligomer mixture is a mixture of chain oligomers having about 4 to 80 carbon atoms (C4 to C80) with an unsaturated double bond at the α-position. In general, the ethylenic oligomer mixture contains a large amount of ethylenic oligomers having relatively small numbers of carbon atoms, such as those having about 4 to 30 carbon atoms, for example, 1-butene (C4), 1-hexene (C6), 1-octene (C8), 1-decene (C10), 1-dodecene (C12), 1-tetradecene (C14), 1-hexadecene (C16), 1-octadecene (C18), 1-eicosene (C20), 1-docosene (C22), 1-tetracosene (C24), 1-hexacosene (C26), 1-octacosene (C28), and 1-triacontesene (C30). By controlling reaction conditions, a larger amount of ethylenic oligomers having desired numbers of carbon atoms can be obtained.

In the present invention, the solution of α-olefin oligomer mixture obtained by polymerization of α-olefin is subsequently subjected to recovery of unreacted α-olefin, deactivation of the catalyst, and deashing treatment. The temperature of the solution after the polymerization reaction is preferably 90 to 150° C., more preferably 100 to 130° C. The organic solvent and unreacted α-olefin are separated and recovered by distillation. The recovered unreacted α-olefin and organic solvent are recycled into the polymerization reaction system.

Subsequently, the catalyst is preferably subjected to deactivation treatment by adjusting the pressure of the treatment system to about 4 kg/cm$^2$·G (0.39 MPa) and introducing a deactivating agent. Examples of the deactivating agent to be used in this process include basic nitrogen compounds, water, alcohols, carboxylic acids, and phenols. Among these, examples of the basic nitrogen compounds include ammonia; and amines such as methylamine, ethylamine, propylamine, butylamine, pentylamine, hexylamine, cyclohexylamine, octylamine, decylamine, aniline, benzylamine, naphthylamine, dimethylamine, diethylamine, dibutylamine, diphenylamine, methylphenylamine, trimethylamine, triethylamine, tributylamine, triphenylamine, pyridine, and picoline.

Figure 1:
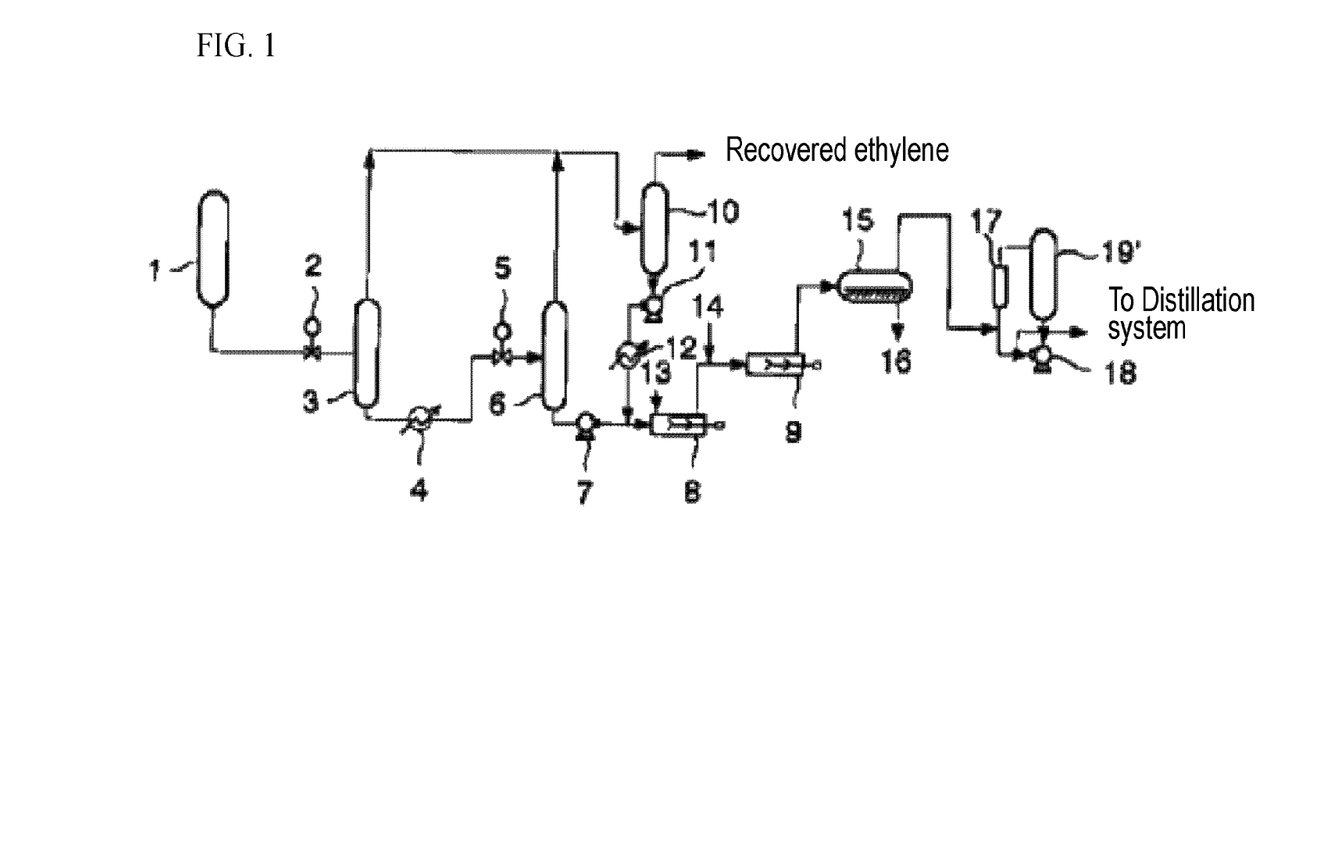
FIG. 1 is a schematic flow chart showing an example of the process for carrying out the present invention.

A preferred mode of production of the α-olefin oligomer mixture is described with reference to FIG. 1. FIG. 1 is an exemplary flow chart for carrying out the present invention. The liquid reaction product produced in a reactor 1 and containing a Ziegler based catalyst, a solvent, unreacted ethylene, and ethylenic oligomers is supplied to a first stage flash tank 3 via a control valve 2, and further to a second stage flash tank 6 via a control valve 5. The liquid product after the first stage flashing is heated in a heat exchanger 4 in order to be kept at a predetermined temperature or higher before being supplied to the second stage flash tank 6. In these flash tanks, unreacted ethylene dissolved in the liquid reaction product is recovered. The liquid reaction product is then sent to a deactivator 8, where the catalyst is deactivated with a deactivating agent 13. A slight amount of light α-olefin accompanying the recovered ethylene is recovered into a pot 10, and sent to the deactivator 8. The resulting product is then sent to a deasher 9, and washed with washing water 14, followed by being sent to a separating tank 15. In the separating tank 15, the product is separated into an oil tank and a water tank, and the water tank is discarded outside the system as waste water 16. The oil tank is sent to a dissolving tank 19 equipped with a heat exchanger 17 and a pump 18, and then heated to allow complete redissolution of the polymer therein, followed by being sent to a distillation system, where the solvent and the ethylenic oligomer are fractionated.

(Distillation Treatment)

The α-olefin oligomer as the objective product in the present invention can be obtained by subjecting a solution containing an α-olefin oligomer mixture to at least a distillation step for separation of the mixture.

The α-olefin oligomer mixture is subjected to distillation treatment to separate α-olefin oligomers having less than n carbon atoms from α-olefin oligomers having n or more carbon atoms. The distillation is preferably carried out in a multistage manner. By the distillation in a multistage manner, individual α-olefin oligomers can be isolated in the order from smaller to larger numbers of carbon atoms, and, as a result, the individual α-olefin copolymers can be utilized as monomers and comonomers for olefin polymers.

The number of carbon atoms n is preferably 20, 22, 24, 26, 28, or 30, more preferably 26 or 30. In general, α-olefin oligomers having 26 or more carbon atoms have high boiling points, and are therefore less likely to evaporate even under reduced pressure. Although the evaporation is more likely to occur at an increased temperature, the temperature control has limitation taking degradation of α-olefin into account. Therefore, further distillation separation of individual α-olefin polymers is difficult for α-olefin oligomers having 26 or more carbon atoms (C26+), α-olefin oligomers having 28 or more carbon atoms (C28+), or α-olefin oligomers having 30 or more carbon atoms (C30+). For C26+, it had been tentatively confirmed that a distillation residue of C30+ can be obtained by distillation separation of a mixture of C26 and C28 under controlled distillation conditions. However, the control of the conditions is actually difficult.

Accordingly, with respect to C26+ (or C30+) ethylenic oligomers as a distillation residue, by separating high molecular weight molecules therefrom by the later-mentioned method to lower the cloud point, individual ethylenic oligomers having less than 26 carbon atoms (or less than 30 carbon atoms) can be utilized as a starting monomer material for olefin polymers, and ethylenic oligomers having 26 or more carbon atoms (or 30 or more carbon atoms) can be utilized as a wax.

Figure 2:
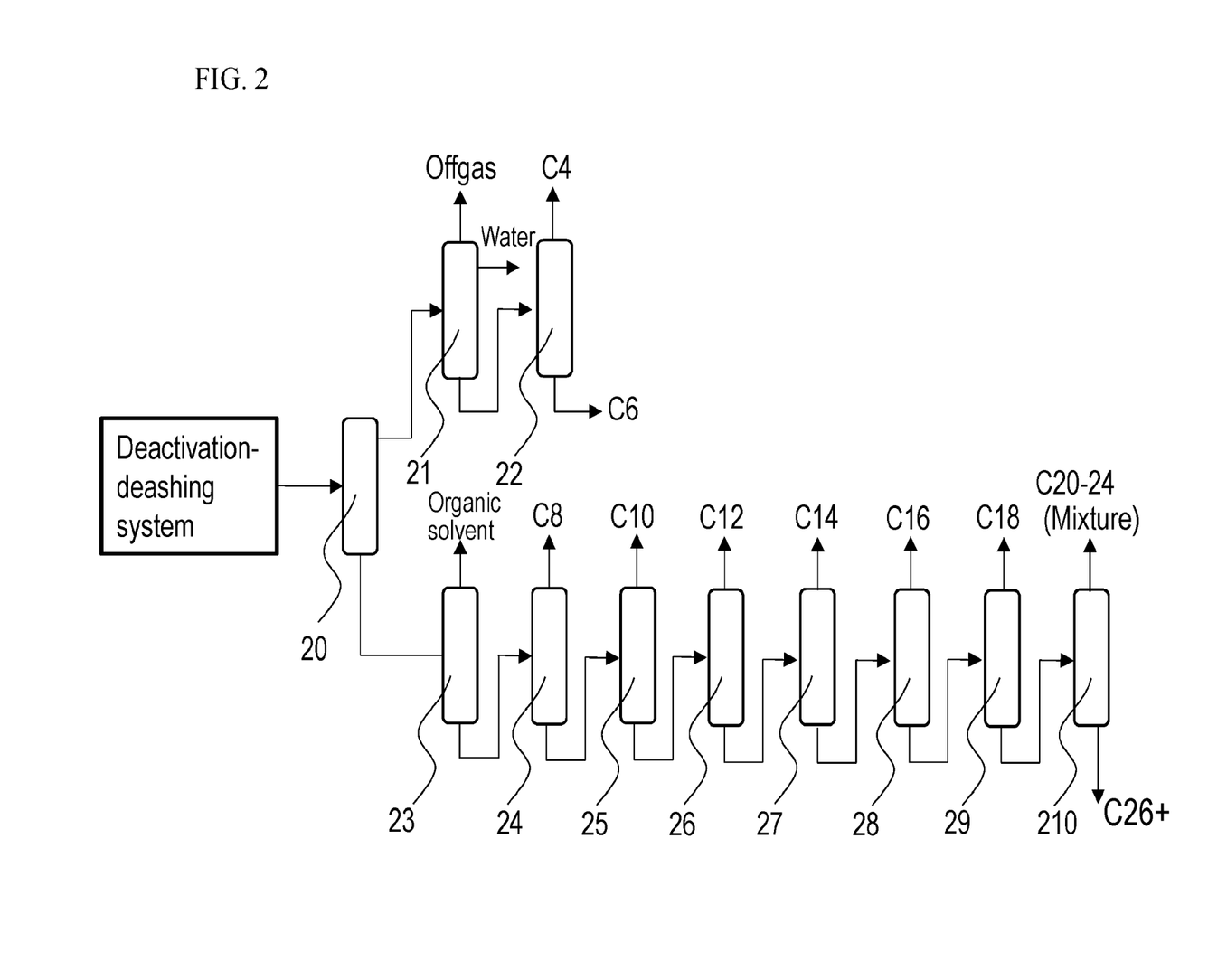
FIG. 2 is a schematic flow chart showing an example of the process for carrying out distillation in the present invention.

<Example of Distillation Flow 1 (n=26) FIG. 2>

Multistage distillation treatment of the ethylenic oligomer mixture obtained by polymerization of ethylene as an α-olefin is concretely described below with reference to FIG. 2.

FIG. 2 is a schematic flow chart for a method in which distillation separation of ethylenic oligomers having less than 26 carbon atoms in an ethylenic oligomer mixture is carried out to obtain a distillation residue containing α-olefin oligomers having 26 or more carbon atoms.

A solution of α-olefin oligomer mixture after deashing treatment is introduced into a first distillation column 20, a liquid containing as a major component α-olefin that is C6 and lower ethylenic oligomers is withdrawn at the top, and a liquid containing as major components α-olefin that is C8 and higher ethylenic oligomers, and an organic solvent, is obtained at the bottom. The top liquid in the first distillation column 20 is introduced into a second distillation column 21, offgas and water are withdrawn at the top, C4 and higher α-olefins obtained at the bottom are introduced into a third distillation column 22, and C4 and C6 α-olefins are obtained at the top and at the bottom, respectively. The bottom liquid in the first distillation column 20 is introduced into a fourth distillation column 23, the organic solvent is obtained at the top, and a liquid containing as a major component α-olefin that is C8 and higher ethylenic oligomers is obtained as the bottom liquid. The bottom liquid in the fourth distillation column 23 is consecutively introduced, in the same manner as described above, into distillation columns 24, 25, 26, 27, 28, 29, and 210, α-olefin polymers as C8, C10, C12, C14, C16, C18, and C20 to C24 (mixture) ethylenic oligomers, respectively, are obtained at the top, and a distillation residue containing C26+ ethylenic oligomers is obtained at the bottom of the final distillation column 210.

Figure 3:
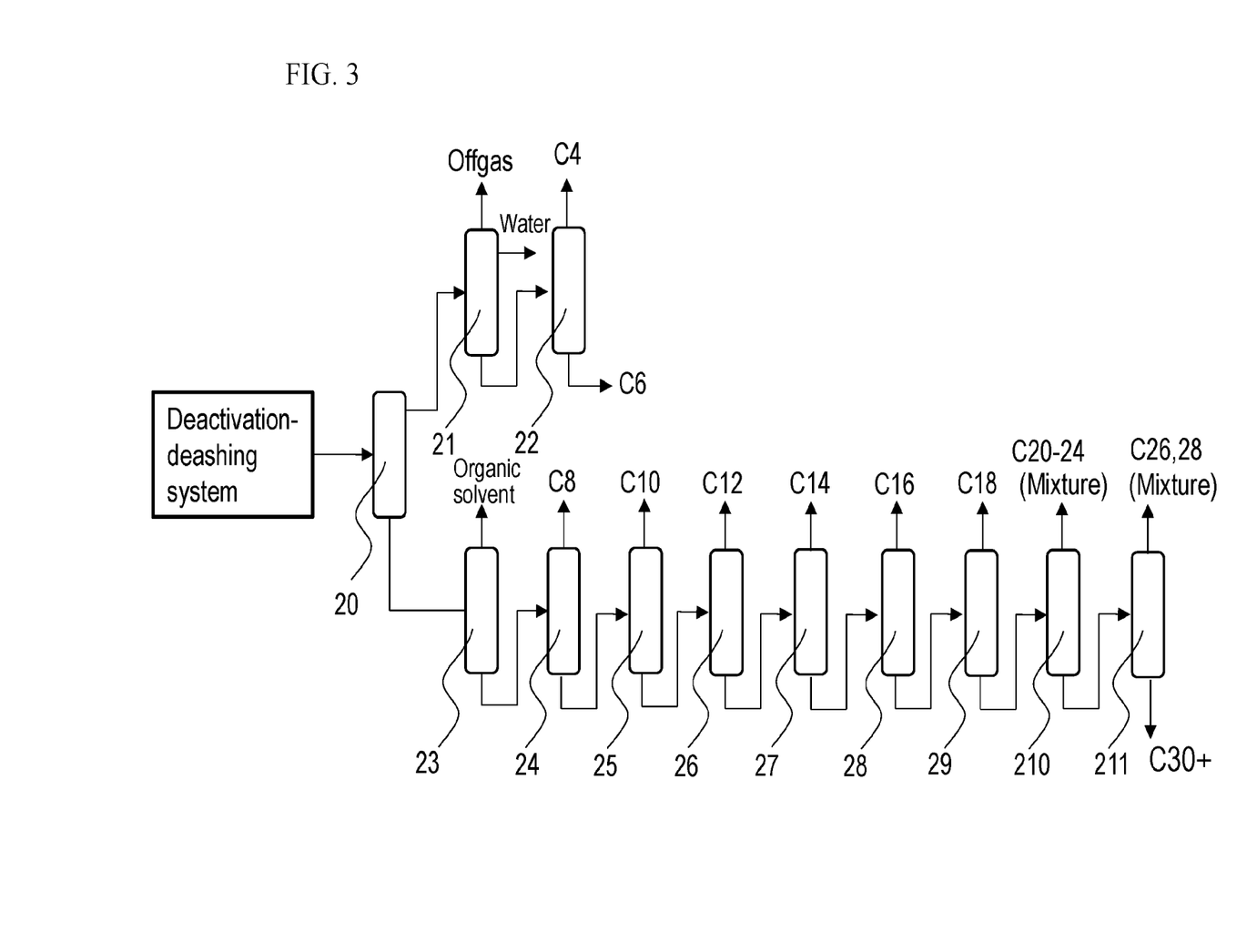
FIG. 3 is a schematic flow chart showing another example of the process for carrying out distillation in the present invention.

<Example of Distillation Flow 2 (n=30) FIG. 3>

FIG. 3 is a schematic flow chart for a method in which distillation separation of ethylenic oligomers having less than 30 carbon atoms in an ethylenic oligomer mixture is carried out to obtain a distillation residue containing α-olefin oligomers having 30 or more carbon atoms.

The flow is the same as the example of distillation flow 1 until obtaining C26+ ethylenic oligomers from the distillation column 210. The bottom liquid in the distillation column 210 is introduced into a distillation column 211, an α-olefin polymer as C26 and C28 (mixture) ethylene oligomers is obtained at the top, and a distillation residue containing C30+ ethylenic oligomers is obtained at the bottom of the final distillation column 211.

The distillation in the present invention is not limited to the modes such as the examples of distillation flow 1 and 2. For example, the number of distillation columns in each of the examples of distillation flow 1 and 2 may be increased or decreased as appropriate, or the distillation does not need to be multistage distillation. For example, the distillation may be a single distillation under conditions that allow separation of C26+ (or C30+) ethylenic oligomers from less than C26 (or less than C30) ethylenic oligomers. However, from the viewpoint of effective use of the ethylenic oligomers separated by the distillation and the ethylenic oligomers contained in the distillation residue, multistage distillation, as in the example of distillation flow 1 or 2, is preferably carried out.

(Step of Removing High Molecular Weight Molecules from Distillation Residue)

In the present invention, a step of removing high molecular weight molecules from the distillation residue containing α-olefin oligomers obtained by the distillation is carried out.

The method for removing the high molecular weight molecules is not limited, and preferably thin film distillation, short-path distillation, or a decanter method.

<Thin Film Distillation>

Thin film distillation is a distillation method in which a raw evaporation material is continuously supplied under reduced pressure onto a plane heated at a certain constant temperature to allow formation of a thin uniform film, and the raw evaporation material is heated only while the material is present on the plane, to allow instantaneous evaporation of a component having a relatively low boiling point, and to recover a component having a relatively high boiling point from the plane. In thin film distillation, a film of the α-olefin oligomers as a raw evaporation material can be formed before the evaporation. Therefore, evaporation of the α-olefin oligomers can be promoted to increase the purification efficiency, and moreover, the thermal history imposed on the α-olefin oligomers can be suppressed.

By recovering the distilled portion obtained by the thin film distillation, α-olefin oligomers from which high molecular weight molecules are removed can be obtained.

From the viewpoint of simple separation (removal) of the high molecular weight molecules, the thin film distillation apparatus preferably has a condenser therein.

The method for the formation of the thin film is not limited, and examples thereof include methods such as a flow-down method, centrifugal method, stirring method, rotary method, blade method, and elevation method. Among these, a rotary method using a wiper or the like is preferred.

The distillation conditions for the thin film distillation are not limited. From the viewpoint of simple separation (removal) of the high molecular weight molecules, the conditions are as described below.

The distillation temperature is preferably 150 to 320° C., more preferably 230 to 320° C., still more preferably 280 to 310° C.

The pressure during the distillation is preferably $1.0 \times 10^{-2}$ to $5.0 \times 10^{-2}$ Torr.

The feeding amount of the α-olefin oligomers as a raw evaporation material is preferably 300 to 600 mL/h, and the rotation speed of the wiper is preferably 50 to 600 rpm. The wiper rotation speed is preferably 350 to 450 rpm in cases of thin film distillation of C26+ ethylenic oligomers, preferably 60 to 220 rpm in cases of thin film distillation of C30+ ethylenic oligomers.

<Short-Path Distillation>

The thin film distillation is preferably short-path distillation.

Short-path distillation allows distillation under medium vacuum (for example, at about $10^2$ Pa to $10^{-1}$ Pa) with a short residence time (for example, several seconds to 1 minute at most), thereby enabling distillation of substances with high boiling points, which is difficult for batch-type short distillation. By the short-path distillation, high molecular weight molecules can be removed as high-boiling-point substances from the distillation residue.

A short-path distillation apparatus at least has an evaporator, condenser, and pressure reduction means (for example, vacuum pump). The evaporator preferably has an evaporation plane, and examples of the evaporation plane include plate-shaped bodies such as rectangular plates and disks; cylindrical bodies; and bottomed containers. The evaporation plane may be, for example, a surface of a plate-shaped body, the inner surface or outer surface of a cylindrical body, or an inner surface of a container. From the viewpoint of forming the thin film of the α-olefin oligomers as a raw evaporation material before the evaporation, the evaporator preferably has, for example, a plate shape or a cylindrical shape.

<Decanter Method>

By using a decanter method, the high molecular weight molecules can be removed. The decanter method in the present invention at least includes a step of dissolving the distillation residue containing α-olefin oligomers under heat in an organic solvent, cooling the resulting solution to allow formation of a precipitate, and then removing the precipitate.

The conditions for the decanter method are not limited as long as the distillation residue can be dissolved by the heating and the precipitation of the high molecular weight molecules occurs by the cooling. From the viewpoint of easily separating (removing) the high molecular weight molecules, the conditions are as described below.

The type of the organic solvent is not limited as long as the distillation residue containing α-olefin oligomers can be dissolved therein. Examples of the organic solvent include aliphatic organic solvents such as octane, decane, dodecane, tetradecane, and hexadecane; aromatic organic solvents such as xylene, ethylbenzene, and toluene; and olefin organic solvents such as 1-octene, 1-decene, 1-dodecene, and 1-tetradecene. Among these, toluene is preferred.

The dissolution is allowed under heat, and the heating temperature is preferably 70 to 130° C., more preferably 80 to 120° C., still more preferably 90 to 110° C.

The retention time under heat is not limited as long as the distillation residue containing α-olefin oligomers can be dissolved. The retention time under heat is preferably 0.5 to 2 hours.

The cooling temperature after the dissolution is preferably 20 to 60° C., more preferably 30 to 50° C., still more preferably 35 to 45° C.

The cooling rate is preferably 0.1 to 5° C./minute, more preferably 0.5 to 1° C./minute.

The retention time after the cooling is preferably 0 to 1 hour, more preferably 0.05 to 0.5 hour.

The precipitate formed by the cooling is removed by, for example, suction filtration. By subjecting the resulting filtrate to evaporation of the solvent under reduced pressure, α-olefin oligomers from which high molecular weight molecules are removed can be obtained.

(High Molecular Weight Molecules)

The distillation residue obtained by the short-path distillation/thin film distillation, or the precipitate formed by the decanter method, is composed of high molecular weight molecules having a weight average molecular weight of 100,000 or more.

The weight average molecular weight is a value determined by GPC, and is measured by the method described in Examples.

(α-Olefin Oligomers from Which High Molecular Weight Molecules Are Removed)

In the present invention, by the method described above, α-olefin oligomers from which high molecular weight molecules are removed, preferably ethylenic oligomers from which high molecular weight molecules are removed, are obtained.

The ethylenic oligomers are preferably C26+ ethylenic oligomers from which high molecular weight molecules are removed, or C30+ ethylenic oligomers from which high molecular weight molecules are removed.

In the case where the step of removing high molecular weight molecules in the present invention is not carried out, the C26+ or C30+ ethylenic oligomers usually contain high molecular weight molecules having a weight average molecular weight of 100,000 or more at about 1000 to 40,000 ppm. By performing the step of removing high molecular weight molecules in the present invention, the amount of high molecular weight molecules having a weight average molecular weight of 100,000 or more can be reduced to 500 ppm or less.

Since the cloud point of the ethylenic oligomers from which high molecular weight molecules are removed as described above is preferably 100° C. or less, more preferably 40 to 90° C., still more preferably 40 to 80° C., the ethylenic oligomers are highly useful as a wax, and can be used for a variety of uses including wax additives, cosmetics, resin lubricants, candles, and PVC lubricants.

EXAMPLES

The present invention is described below in more detail by way of Examples, but the present invention is not limited by the Examples.

[Measurement of Cloud Point]

According to JIS K 2269, the cloud point was measured.

[GPC Measurement]

By gel permeation chromatography (GPC), the weight average molecular weight (Mw) and the molecular weight distribution (Mw/Mn) were determined. In the measurement, the following apparatus and conditions were used to obtain the weight average molecular weight in terms of polystyrene.

<GPC Measurement Apparatus>
Column: TOSO GMKHHR-H (S) HT
Detector: RI detector for liquid chromatography WATERS 150C <Measurement Conditions>
Solvent: 1,2,4-trichlorobenzene
Measurement temperature: 145° C.
Flow rate: 1.0 mL/minute
Sample concentration: 2.2 mg/mL
Injection volume: 160 μL
Calibration curve: Universal Calibration
Analysis program: HT-GPC (Ver. 1.0)

Example 1

[Preparation of Catalyst]

In a 500-mL flask equipped with a stirrer, 25 mmol of zirconium tetrachloride anhydride and 250 mL of dry cyclohexane were introduced under argon atmosphere, and the resulting mixture was stirred for 10 minutes at room temperature. To the mixture, triethylaluminum [$(C_2H_5)_3Al$] was added, and then ethylaluminum sesquichloride [$(C_2H_5)_3Al_2Cl_3$] was added. The amounts of the triethylaluminum and the ethylaluminum sesquichloride were adjusted such that $(C_2H_5)_3Al_2Cl_3/(C_2H_5)_3Al=3.5$ (molar ratio) and $[(C_2H_5)_3Al_2Cl_3+(C_2H_5)_3Al]/ZrCl_4=7$ (molar ratio) were satisfied. After adding all components, the resulting mixture was heated at 70° C. with stirring for 2 hours under argon atmosphere to allow complex formation, thereby preparing a liquid catalyst.

[Oligomerization Reaction]

The reaction was continuously carried out using a complete mixing tank type reactor (internal volume, 1 L). The liquid catalyst was mixed with cyclohexane dried under argon atmosphere, such that the concentration of zirconium tetrachloride was adjusted to 0.08 mmol/L-cyclohexane. Thiophene was then added to the mixture at three times the moles of zirconium tetrachloride, and the resulting mixture was constantly (700 cc/hour) supplied to the reactor. The level in the reactor was set to 500 cc, and the residence time was set to about 43 minutes based on the solvent. The reaction was carried out at 120° C. at 65 kg/cm²·G (6.4 MPa) with stirring at 500 rpm. High-purity ethylene gas was continuously supplied such that a reaction pressure of 65 kg/cm²·G was maintained. The conditions and the results are shown in Table 1.

TABLE 1

| | | | |
|---|---|---|---|
| ZrCl$_4$ | | (mmol/hour) | 0.08 |
| Ethylaluminum sesquichloride | | (mmol/hour) | 0.436 |
| Triethylaluminum | | (mmol/hour) | 0.124 |
| Cyclohexane | | (cc/hour) | 700 |
| Reaction temperature | | (° C.) | 120 |
| Reaction pressure | | (kg/cm² · G) | 65 |
| Reaction time | | (minutes) | 43 |
| Catalytic activity | | (kg/g · ZrCl$_4$) | 12.6 |
| Ethylene oligomer | C4 | (mass %) | 14.9 |
| | C6 | (mass %) | 15.4 |
| | C8 | (mass %) | 14.1 |
| | C10 to 18 | (mass %) | 41.3 |
| | C20 and higher | (mass %) | 14.3 |
| | C18 purity | | 94.5 |

[Deactivation Treatment of Catalyst]

Deactivation treatment of the catalyst was carried out by continuously supplying the liquid reaction product obtained in the polymerization reaction to a deactivating tank under the following conditions: cyclohexane, 546 g/hour (700 cc/hour); ethylenic oligomer, 225 g/hour; 771 g/hour in total. As a deactivating agent, an aqueous ammonia having a concentration of 10% by weight was supplied at 28 g/hour. In the deactivating tank, a pressure of 4 kg/cm²·G (0.39 MPa) and a temperature of 100° C. were maintained, and stirring was carried out at 700 rpm.

The liquid product after the deactivation treatment was filtered through a filter paper to separate wax. The resulting filtrate was washed twice with two volumes of ion-exchanged water, and then dried over anhydrous potassium carbonate. A colorless, transparent liquid reaction product was obtained as a result, and the product was analyzed by gas chromatography to determine the distribution and purity of the ethylenic oligomer as the objective product. The product distribution was found by calculation through Schultz-Flory distribution from the analysis result of gas chromatography for C10 and higher, based on the operational loss.

[Distillation Operation 1]

The oligomerization reaction liquid subjected to the catalyst deactivation as obtained above was subjected to distillation separation as follows.

The oligomerization reaction liquid was introduced into an Oldershaw distillation unit (first distillation column 20). During the operation, the pressure at the top was kept at normal pressure; the temperature at the top was kept at 66.1° C.; and the temperature at the bottom was kept at 90.7° C. A liquid containing as major components C6 and lower ethylenic oligomers was withdrawn at the top, while a liquid containing as major components C8 and higher ethylenic oligomers as well as most of the cyclohexane was obtained at the bottom.

The bottom liquid from the first distillation column 20 was introduced into an Oldershaw distillation unit (fourth distillation column 23). During the operation, the pressure at the top was kept at normal pressure; the temperature at the top was kept at 80.0° C.; and the temperature at the bottom was kept at 170.9° C. A liquid containing as a major component cyclohexane was withdrawn at the top, while a liquid containing as major components C8 and higher ethylenic oligomers was obtained at the bottom.

The bottom liquid from the fourth distillation column 23 was introduced into an Oldershaw distillation unit (fifth distillation column 24). A liquid containing as a major component C8 was withdrawn at the top, while a liquid containing as major components C10 and higher ethylenic oligomers was obtained at the bottom.

The bottom liquid from the fifth distillation column 24 was introduced into an Oldershaw distillation unit (sixth distillation column 25). A liquid containing as a major component C10 was withdrawn at the top, while a liquid containing as major components C12 and higher ethylenic oligomers was obtained at the bottom.

The bottom liquid from the sixth distillation column 25 was introduced into an Oldershaw distillation unit (seventh distillation column 26). A liquid containing as a major component C12 was withdrawn at the top, while a liquid containing as major components C14 and higher ethylenic oligomers was obtained at the bottom.

The bottom liquid from the seventh distillation column 26 was introduced into an Oldershaw distillation unit (eighth distillation column 27). A liquid containing as a major component C14 was withdrawn at the top, while a liquid containing as major components C16 and higher ethylenic oligomers was obtained at the bottom.

The bottom liquid from the eighth distillation column 27 was introduced into an Oldershaw distillation unit (ninth distillation column 28). A liquid containing as a major component C16 was withdrawn at the top, while a liquid containing as major components C18 and higher ethylenic oligomers was obtained at the bottom.

The bottom liquid from the ninth distillation column 28 was introduced into an Oldershaw distillation unit (tenth distillation column 29). A liquid containing as a major component C18 was withdrawn at the top, while a liquid containing as major components C20 and higher ethylenic oligomers was obtained at the bottom.

The bottom liquid from the tenth distillation column 29 was introduced into an Oldershaw distillation unit (eleventh distillation column 210). A liquid containing as major components C20, C22, and C24 was withdrawn at the top, while a liquid containing as major components C26 and higher ethylenic oligomers (C26+) was obtained at the bottom.

From the liquid containing as major components C26 and higher ethylenic oligomers (C26+), the solvent was removed by evaporation, to obtain the C26 and higher ethylenic oligomers (C26+) in the form of a solid. The resulting C26+ showed a measured cloud point of 120° C. or more.

[Thin Film Distillation of C26+]

The solution containing C26+ as major components, obtained by the distillation operation 1, was introduced into a thin film distillation apparatus ("Type KDL5", manufactured by Pfintech Inc.) equipped with an internal condenser at a feed rate of 450 mL/hour. The solution containing C26+ as major components was applied to the inner surface of the main body of the distillation apparatus using a wiper (rotation speed, 400 rpm), to allow formation of a thin film. Subsequently, the thin film formed was heated at 170° C. using a heater under reduced pressure (1.6 to $1.8 \times 10^{-2}$ Torr). The evaporated portion was cooled by the internal condenser to flow down into a distilled portion receiver. On the other hand, the distillation residue was allowed to flow along the inner surface of the main body into a residue receiver. The amount of the distilled portion was 111.5 g, and the amount of the distillation residue was 109.5 g (Table 2). The distilled portion was recovered, and the solvent was removed therefrom. The resulting product showed a measured cloud point of 85° C. or less. According to GPC measurement, the amount of high molecular weight components having a weight average molecular weight of 100,000 or more in the distilled portion was 500 ppm or less.

Examples 2 to 9

The solution containing C26+ as major components, obtained by the distillation operation 1, was subjected to thin film distillation using a thin film distillation apparatus ("Type KDL5", manufactured by Pfintech Inc.) equipped with an internal condenser in the same manner as in Example 1 except that the feed rate, wiper rotation speed, pressure, and temperature conditions were changed according to Table 2. As a result, the distilled portion showed a measured cloud point of 85° C. or less in all cases. The amounts of the distilled portion and the distillation residue were as shown in Table 2.

Example 10

The preparation of the catalyst, the polymerization reaction, and the deactivation treatment of the catalyst were carried out in the same manner as in Example 1. The oligomerization reaction liquid subjected to the catalyst deactivation as obtained above was subjected to distillation separation as follows.

[Distillation Operation 2]

The same operation as the distillation operation 1 was carried out until obtaining the bottom liquid from the eleventh distillation column 210.

The bottom liquid from the eleventh distillation column 210 was introduced into an Oldershaw distillation unit (twelfth distillation column 211). A liquid containing as major components C26 and C28 was withdrawn at the top, while a liquid containing as major components C30 and higher ethylenic oligomers (C30+) was obtained at the bottom.

From the liquid containing C30+ as major components, the solvent was removed by evaporation, to obtain the C30+ in the form of a solid. The resulting C30+ showed a measured cloud point of 120° C. or more.

[Thin Film Distillation of C30+]

The solution containing C30+ as major components, obtained by the distillation operation 2, was introduced into a thin film distillation apparatus ("Type KDL5", manufactured by Pfintech Inc.) equipped with an internal condenser at a feed rate of 450 mL/hour. The solution containing C30+ as major components was applied to the inner surface of the main body of the distillation apparatus using a wiper (rotation speed, 200 rpm), to allow formation of a thin film. Subsequently, the thin film formed was heated at 240° C. using a heater under reduced pressure (4.3 to $4.5 \times 10^{-2}$ Torr). The evaporated portion was cooled by the internal condenser to flow down into a distilled portion receiver. On the other hand, the distillation residue was allowed to flow along the inner surface of the main body into a residue receiver. The amount of the distilled portion was 117.1 g, and the amount of the distillation residue was 107.3 g (Table 3). The distilled portion was recovered, and the solvent was removed therefrom. The resulting product showed a measured cloud point of 85° C. or less. According to GPC measurement, the amount of high molecular weight components having a weight average molecular weight of 100,000 or more in the distilled portion was 500 ppm or less.

Examples 11 and 12

The solution containing C30+ as major components, obtained by the distillation operation 2, was subjected to thin film distillation using a thin film distillation apparatus ("Type KDL5", manufactured by Pfintech Inc.) equipped with an internal condenser in the same manner as in Example 10 except that the pressure and temperature conditions were changed according to Table 3. As a result, the distilled portion showed a measured cloud point of 85° C. or less in all cases. The amounts of the distilled portion and the distillation residue were as shown in Table 3.

TABLE 2

|  | Temperature (° C.) | Pressure (Torr) | Distillation (g) | Residue (g) | Distillation (%) | Residue (%) | Recovery (%) |
|---|---|---|---|---|---|---|---|
| Example 1 | 170 | 1.6-1.8 × $10^{-2}$ | 111.5 | 109.5 | 50.5 | 49.5 | 50.5 |
| Example 2 | 180 | 2.4-2.8 × $10^{-2}$ | 131.3 | 96.8 | 57.5 | 42.5 | 57.5 |
| Example 3 | 190 | 1.9-2.0 × $10^{-2}$ | 141.2 | 77.5 | 64.5 | 35.5 | 64.5 |
| Example 4 | 200 | 1.8-1.9 × $10^{-2}$ | 154.2 | 63.7 | 70.8 | 29.2 | 70.8 |
| Example 5 | 220 | 2.3-4.2 × $10^{-2}$ | 154.3 | 36.6 | 80.8 | 19.2 | 80.8 |
| Example 6 | 240 | 2.8-3.6 × $10^{-2}$ | 160.8 | 25.8 | 86.2 | 13.8 | 86.2 |
| Example 7 | 260 | 2.2-2.4 × $10^{-2}$ | 174.3 | 19.3 | 90.0 | 10.0 | 90.0 |
| Example 8 | 280 | 3.1-4.0 × $10^{-2}$ | 204.2 | 16.2 | 92.7 | 7.3 | 92.7 |
| Example 9 | 300 | 1.5-2.0 × $10^{-2}$ | 499.8 | 20.2 | 96.1 | 3.9 | 96.1 |

TABLE 3

|  | Temperature (° C.) | Pressure (Torr) | Distillation (g) | Residue (g) | Distillation (%) | Residue (%) | Recovery (%) |
|---|---|---|---|---|---|---|---|
| Example 10 | 240 | 4.3-4.5 × $10^{-2}$ | 117.1 | 107.3 | 52.2 | 47.8 | 52.2 |
| Example 11 | 260 | 3.3-3.6 × $10^{-2}$ | 126.0 | 95.8 | 56.8 | 43.2 | 56.8 |
| Example 12 | 300 | 4.6-4.7 × $10^{-2}$ | 156.9 | 95.0 | 62.3 | 37.7 | 62.3 |

Example 13

To 300 mL of toluene, 20.4 g of the C26+ obtained by the distillation operation 1 in Example 1 was added, and the resulting mixture was heated at 100° C. to allow complete dissolution of the C26+. Subsequently, the temperature was decreased slowly (at a cooling rate of 0.6° C./minute) to 40° C. in an oil bath. The mixture was then kept at 40° C. for 5 minutes, and the resulting precipitate was removed by suction filtration using a membrane filter (3 μm). Toluene in the resulting filtrate was removed using an evaporator and by blowing nitrogen, to obtain 19.7 g of C26+ from which high molecular weight molecules were removed. The C26+ from which high molecular weight molecules were removed had a cloud point of about 80° C.

REFERENCE SIGNS LIST

1: Reactor
3, 6: Flash tank
7, 11, 18: Pump
8: Deactivator
9: Deasher
10: Pot
4, 17: Heat exchanger
19: Dissolving tank
20 to 29, 210, 211: Distillation column

The invention claimed is:

1. A method for producing an α-olefin oligomer, the method comprising:
    subjecting ethylene to an oligomerization reaction to produce an α-olefin oligomer mixture;
    carrying out a distillation separation of an α-olefin oligomer having less than n carbon atoms in the α-olefin oligomer mixture to obtain a distillation residue containing an α-olefin oligomer having n or more carbon atoms, where n is 26 or 30; and then
    removing a high molecular weight molecule having a weight average molecular weight of 100,000 or more from the distillation residue such that the distillation residue, after the removing of the high molecular weight molecule, has a cloud point, measured according to JIS K 2269, of 100° C. or less.

2. The method according to claim 1, wherein the oligomerization reaction of ethylene is carried out in an organic solvent in the presence of a Ziegler-based catalyst.

3. The method according to claim 1, wherein the number of carbon atoms n is 26.

4. The method according to claim 1, wherein the removing of the high molecular weight molecule is carried out by thin film distillation of the distillation residue.

5. The method according to claim 4, wherein the thin film distillation is carried out with a distillation temperature of from 150 to 320° C. and a pressure of from $1.0 \times 10^{-2}$ to $5.0 \times 10^{-2}$ Torr.

6. The method according to claim 4, wherein the thin film distillation is a short-path distillation.

7. The method according to claim 1, wherein the removing of the high molecular weight molecule is carried out by
    dissolving the distillation residue in an organic solvent under heat to obtain a solution,
    cooling the solution such that a precipitate is formed, and then
    removing the precipitate.

8. The method according to claim 7, wherein
    a heating temperature during the dissolving is from 70 to 130° C.,
    a retention time under the heat is from 0.5 to 2 hours,
    a cooling rate during the cooling is from 0.1 to 5° C./minute, and
    a retention time after the cooling is from 0 to 1 hour.

9. The method according to claim 1, wherein the removing of the high molecular weight from the distillation residue is performed such that the distillation residue, after the removing of the high molecular weight molecule, includes the high molecular weight molecule in an amount of 500 ppm or less.

10. The method according to claim 1, wherein the distillation residue, before the removing of the high molecular weight molecule, includes the high molecular weight molecule in an amount of 1,000 ppm to 40,000 ppm.

11. The method according to claim 1, wherein the number of carbon atoms n is 30.

* * * * *